(12) United States Patent
Huerta et al.

(10) Patent No.: US 7,416,719 B2
(45) Date of Patent: *Aug. 26, 2008

(54) SUNSCREEN COMPOSITIONS

(75) Inventors: Jose L. Huerta, Cedar Grove, NJ (US); James Sanogueira, Suffern, NY (US); Jennifer Fuller, Mahway, NJ (US)

(73) Assignee: Playtex Products, Inc., Westport, CT (US)

( * ) Notice: Subject to any disclaimer, the term of this patent is extended or adjusted under 35 U.S.C. 154(b) by 811 days.

This patent is subject to a terminal disclaimer.

(21) Appl. No.: 10/836,308

(22) Filed: Apr. 30, 2004

(65) Prior Publication Data

US 2004/0247543 A1 Dec. 9, 2004

Related U.S. Application Data

(63) Continuation-in-part of application No. 09/957,920, filed on Sep. 21, 2001, now Pat. No. 6,830,746.

(51) Int. Cl.
| A61Q 17/04 | (2006.01) |
| A61Q 17/00 | (2006.01) |
| A61Q 19/04 | (2006.01) |
| A61Q 19/00 | (2006.01) |
| A61K 8/02  | (2006.01) |
| C07G 3/00  | (2006.01) |

(52) U.S. Cl. .......................... 424/59; 424/60; 424/400; 424/401; 514/937; 514/938; 514/939; 514/943; 536/1.1; 536/4.1

(58) Field of Classification Search .................. 424/59, 424/60, 400, 401; 514/937, 938, 939; 536/1.1, 536/4.1
See application file for complete search history.

(56) References Cited

U.S. PATENT DOCUMENTS

| 4,656,029 A | 4/1987 | Grollier et al. ................. 424/47 |
| 5,032,390 A | 7/1991 | Iwaya et al. ................... 424/59 |
| 5,093,107 A | 3/1992 | Matravers ..................... 424/59 |
| 5,208,011 A | 5/1993 | Vaughan ....................... 424/59 |
| 5,208,013 A | 5/1993 | Klein ........................... 424/59 |
| 5,306,486 A | 4/1994 | McCook et al. ................ 424/59 |
| 5,372,805 A | 12/1994 | Finkel et al. .................... 424/59 |
| 5,417,961 A | 5/1995 | Nearn et al. ................... 424/59 |
| 5,486,631 A | 1/1996 | Mitchnick et al. .............. 556/10 |
| 5,543,136 A | 8/1996 | Aldous .......................... 424/59 |
| 5,554,374 A | 9/1996 | Olivier-Terras ............. 424/401 |
| 5,571,503 A | 11/1996 | Mausner ........................ 424/59 |
| 5,614,178 A | 3/1997 | Bloom et al. .................. 424/60 |
| 5,658,580 A | 8/1997 | Mausner ...................... 424/401 |
| 5,667,765 A | 9/1997 | Hansenne et al. ............... 424/59 |
| 5,672,337 A | 9/1997 | Ascione et al. ................. 424/59 |
| 5,676,934 A | 10/1997 | Siegfried ....................... 424/59 |
| 5,725,844 A | 3/1998 | Gers-Barlag et al. ........... 424/59 |
| 5,730,993 A | 3/1998 | Allard et al. ................. 424/401 |
| 5,733,531 A | 3/1998 | Mitchnick et al. ............. 424/59 |
| 5,770,183 A | 6/1998 | Linares ......................... 424/59 |
| 5,776,438 A | 7/1998 | Tokue et al. ................... 424/59 |
| 5,788,954 A | 8/1998 | Bonda et al. ................... 424/59 |
| 5,804,168 A | 9/1998 | Murad ........................... 424/59 |
| 5,827,508 A | 10/1998 | Tanner et al. .................. 424/59 |
| 5,843,411 A | 12/1998 | Hernandez et al. ............. 424/59 |
| 5,851,544 A | 12/1998 | Penska et al. ................ 424/401 |
| 5,891,452 A | 4/1999 | Sebillote-Arnaud et al. .. 424/401 |
| 5,902,591 A | 5/1999 | Herstein ...................... 424/401 |
| 5,916,542 A | 6/1999 | Fossati ......................... 424/59 |
| 5,916,544 A | 6/1999 | Liu et al. ........................ 424/59 |
| 5,922,331 A | 7/1999 | Mausner ...................... 424/401 |
| 5,948,416 A | 9/1999 | Wagner et al. ............... 424/401 |
| 5,951,990 A | 9/1999 | Ptchelintsev ................ 424/401 |
| 5,961,961 A | 10/1999 | Dobkowski et al. ........... 424/59 |
| 5,968,529 A | 10/1999 | Horino et al. ................ 424/401 |
| 5,976,513 A | 11/1999 | Robinson ...................... 424/59 |
| 5,976,555 A | 11/1999 | Liu et al. ..................... 424/401 |
| 6,015,548 A | 1/2000 | Siddiqui et al. ................ 424/59 |
| 6,024,941 A | 2/2000 | Yanagida et al. .............. 424/59 |
| 6,036,945 A | 3/2000 | Deblasi et al. ................. 424/59 |
| 6,039,935 A | 3/2000 | Mohammadi ................. 424/59 |
| 6,043,204 A | 3/2000 | Kaufman et al. ............ 510/130 |
| 6,048,517 A | 4/2000 | Kaplan ........................ 424/60 |
| 6,066,327 A | 5/2000 | Gubernick et al. .......... 424/401 |
| 6,068,848 A | 5/2000 | Gubernick et al. .......... 424/401 |
| 6,071,501 A | 6/2000 | Robinson ...................... 424/59 |
| 6,090,369 A | 7/2000 | Stewart ......................... 424/59 |
| 6,110,477 A | 8/2000 | Hernandez et al. .......... 424/401 |
| 6,123,928 A | 9/2000 | Sovak et al. ................... 424/59 |

(Continued)

OTHER PUBLICATIONS

Manufacture's Technical Bulletin, Montanov* 82—A Range of Glucolipid Emulsifier and Co-Emulsifiers.

(Continued)

*Primary Examiner*—Shelley A. Dodson
(74) *Attorney, Agent, or Firm*—Ohlandt, Greeley, Ruggiero & Perle, L.L.P.

(57) ABSTRACT

The present invention is a sunscreen composition that has at least one sunscreen agent and at least one glucoside emulsifier. The composition also has water. Preferably, the sunscreen composition also has at least one of the following additional components: an emulsifier other than glucoside, emollient, skin-feel additive, moisturizing agent, film former/waterproofing agent, pH adjuster/chelating agent, preservative, or any combinations thereof. The composition is a stable oil-in-water emulsion.

38 Claims, No Drawings

U.S. PATENT DOCUMENTS

| | | | |
|---|---|---|---|
| 6,130,254 A | 10/2000 | Fisher et al. | 514/725 |
| 6,132,737 A | 10/2000 | Wolf et al. | 424/401 |
| 6,153,205 A | 11/2000 | Boussouira et al. | 424/401 |
| 6,153,208 A | 11/2000 | McAtee et al. | 424/402 |
| 6,162,450 A | 12/2000 | Ptchelintsev et al. | 424/401 |
| 6,171,580 B1 | 1/2001 | Katsuyama et al. | 424/59 |
| 6,171,602 B1 | 1/2001 | Roman | 424/401 |
| 6,830,746 B2 * | 12/2004 | SaNogueira et al. | 424/59 |

OTHER PUBLICATIONS

Manufacture's Technical Bulletin, Montanov* 82—Glucolipid O/W Emulsifier of Vegetable Origin.

* cited by examiner

SUNSCREEN COMPOSITIONS

RELATED APPLICATIONS

This application is a continuation-in-part of U.S. application Ser. No. 09/957,920, filed on Sep. 21, 2001, now U.S. Pat. No. 6,830,746 which is incorporated herein in its entirety.

BACKGROUND OF THE INVENTION

I. Field of the Invention

The present invention relates to sunscreen compositions. More particularly, the present invention relates to sunscreen compositions that have enhanced sensory properties when applied.

II. Description of the Related Art

Sunscreen compositions are applied to the skin to protect the skin from the sun's ultraviolet rays that can lead to erythema, a reddening of the skin also known as sunburn. Sunlight or ultraviolet radiation in the UV-B range has a wavelength of 290 nm to 320 nm and is known to be the primary cause of sunburn. Ultraviolet rays at a wavelength of 320 nm to 400 nm, known as UV-A radiation, produces tanning of the skin. However, in the process of doing so, the UV-A rays can damage or harm the skin.

Besides the immediate malady of sunburn, excessive sunlight exposure can lead to skin disorders. For instance, prolonged and constant exposure to the sun may lead to actinic keratoses and carcinomas. Another long-term effect is premature aging of the skin. This condition is characterized by skin that is wrinkled, cracked and has lost its elasticity.

As stated above, sunscreens are typically formulated with the goal of inhibiting skin damage from the sun's rays. The sunscreen composition filters or blocks the harmful UV-A and UV-B rays that can damage and harm the skin. It is believed that sunscreen agents accomplish this by absorbing the UV-A and/or UV-B rays.

In general, sunscreen compositions are oil-in-water emulsions. In this system, the UV-absorbing compounds are typically incorporated into the oil phase.

Consumers consider many factors when purchasing a sunscreen product, such as, the sun protection factor (SPF), how durable the product is after applying it over the skin, the shelf life of the product, and product form (i.e., lotions, gels, creams, and sprays). Another important and influential property of a sunscreen product considered by a consumer is how the product feels and how well it spreads over the skin. Typically, consumers want a sunscreen that feels soft and silky and can be applied in a smooth, continuous film over the skin. Ultimately, product feel could determine whether the consumer decides to purchase the product.

The sunscreen compositions of the present invention provide the user with an enhanced soft, silky feel when applied to skin while still providing superior protection from damaging ultraviolet light.

SUMMARY OF THE INVENTION

It is an object of the present invention to provide a sunscreen composition that can be effectively applied as a lotion.

It is another object of the present invention to provide such a sunscreen composition that has an enhanced soft, silky feel when applied to the skin.

It is still another object of the present invention to provide such a sunscreen composition that spreads uniformly over the skin.

It is yet another object of the present invention to provide such a sunscreen composition that is a stable oil-in-water emulsion.

To accomplish the foregoing objects and advantages, the present invention, in brief summary, is a sunscreen composition that has at least one sunscreen agent, at least one glucoside emulsifier, and water. Preferably, the sunscreen composition also has at least one of the following additional components: an emulsifier other than glucoside, emollient, skin-feel additive, moisturizing agent, film former/waterproofing agent, pH adjuster/chelating agent, preservative, or any combinations thereof.

DETAILED DESCRIPTION OF THE INVENTION

The present invention is a sunscreen composition that is provided as a stable oil-in-water emulsion. The composition has at least one sunscreen agent and at least one glucoside emulsifier. The composition also has water. Preferably, the sunscreen composition also has one or more of the following additional components: an emulsifier other than glucoside, emollient, skin-feel additive, moisturizing agent, film former/waterproofing agent, pH adjuster/chelating agent, preservative, or any combinations thereof.

The sunscreen composition of the present invention is uniquely formulated to provide an enhanced feeling of softness and silkiness when the sunscreen composition is applied to the skin. Moreover, the composition is capable of being easily and uniformly applied over the skin. These enhanced properties are achieved, in large part, by formulating the sunscreen composition as a stable oil-in-water emulsion, where the oil phase has an amount of glucoside emulsifier so that the unexpected soft, silky properties are realized when the sunscreen is applied to the skin.

The one or more sunscreen agents that can be used in the present invention must be capable of absorbing or blocking the harmful effects of ultraviolet radiation. In addition, they must be non-toxic and non-irritating when applied to the skin. Suitable sunscreen agents that may be used in the sunscreen composition include, for example, para-aminobenzoic acid (PABA), butyl methoxydibenzoylmethane (avobenzone), benzophenone-1, benzophenone-2, benzophenone-3, benzophenone-4, benzophenone-6, benzophenone-8, benzophenone-12, methoxycinnamate, ethyl dihydroxypropyl-PABA, glyceryl PABA, homosalate, methyl anthranilate, octocrylene, octyl dimethyl PABA, octyl methoxycinnamate, octyl salicylate, PABA, 2-phenylbenzimidazole-5-sulphonic acid, triethanolamine salicylate, 3-(4-methylbenzylidene)-camphor, red petrolatum, zinc oxide, titanium dioxide, 3-(4-methylbenzyldine)boran-2-one(methylbenzindinecamphor), benzotriazole, phenylbenzimidazole-5-sulfonic acid, methylene bis-benzotrizolyl tetramethylbutyl phenol, or any mixtures or combinations thereof.

The preferred sunscreen agents are avobenzone, benzophenone-3, octyl methoxycinnamate, octyl salicylate, homosalate, zinc oxide, octocrylene, avobenzone, titanium dioxide, or any mixtures thereof.

The one or more sunscreen agents are included in a present composition at about 1 weight percent (wt. %) to about 40 wt. % of the total weight of the composition. The amount of sunscreen agent in the composition will vary in the above range depending on the sun protection factor (SPF) desired. The higher the SPF, the greater the total amount of sunscreen agent. Preferably, the one or more sunscreen agents are at about 4 wt. % to about 35 wt. % based on the total weight of the composition to achieve a SPF of about 2 to about 50.

As noted above, it has been discovered that the inclusion of one or more glucoside emulsifiers in the sunscreen compositions of the present invention results in compositions that have an enhanced soft, silky feel when applied to the skin. Preferably, the one or more glucoside emulsifiers are selected from the following: alkyl glucoside, cetearyl glucoside, cocoyl glucoside, cocoyl ethyl glucoside, disodium coco-glucoside citrate, disodium coco-glucoside sulfosuccinate, lauroyl ethyl glucoside, myristoyl ethyl glucoside, octyl dimethicone ethoxy glucoside, oleoyl ethyl glucoside, sodium coco-glucoside tartrate, or any mixtures thereof. In one embodiment, the glucoside emulsifier is cocoyl glucoside mixed with cetearyl alcohol. A mixture of cocoyl glucoside with cetearyl alcohol is available from SEPPIC under the tradename MONTANOV® 82. It has been unexpectedly found that the inclusion of MONTANOV® 82 imparts an exceptional and enhanced soft, silky feel to a user's skin when a sunscreen composition of the present invention is applied. In another embodiment the glucoside emulsifier is an alkyl glucoside. Most preferably, the glucoside emulsifier is lauryl glucoside. It has been unexpectedly found that the inclusion of lauryl glucoside imparts an exceptional and enhanced soft, silky feel to a user's skin when a sunscreen composition of the present invention is applied.

Lauryl glucoside is an inexpensive emulsifier typically used as a cleanser. However, it has been unexpectedly found that lauryl glucoside imparts a quick-absorbing, non-greasy, elegant feel to the skin when used in sunscreen compositions. Further, it has been found that the use of lauryl glucoside in sunscreen compositions allows for the formulation of emulsions with smaller particle sizes as compared to traditional emulsifiers. A sunscreen composition with a smaller emulsion particle size demonstrates a greater SPF value than a similarly formulated composition with a larger emulsion particle size.

Additionally, lauryl glucoside is more efficient as an emulsifier in sunscreen compositions than traditional emulsifiers in that a smaller amount of lauryl glucoside can maintain a higher oil phase content without the negative impact of higher emulsifier content. One drawback of high emulsifier content is the difficulty in formulating waterproof sunscreen compositions. After a sunscreen emulsion is applied to the skin, emulsifier components tend to become part of the oil phase, which remains on the skin. If there is excess emulsifier unbound in the oil phase, it more readily reconstitutes into an emulsion when water comes in contact with the skin. Thus, this emulsifier allows for oil phase active ingredients to be washed off the skin. Having a minimum amount of emulsifier necessary to maintain a given oil phase in a sunscreen composition minimizes this wash off effect and, thus, keeps the sunscreen actives on the skin.

Further, with less emulsifier it is possible to use less waterproofing agent/filmer or not as efficient waterproofing agent/film former than would otherwise be necessary to achieve a certain level of waterproofing. The not as efficient waterproofing agent/film former is normally less expensive than higher efficiency waterproofing agent/film former.

The amount of glucoside emulsifier present in a sunscreen composition of the present invention is about 0.05 wt. % to about 10 wt. % of the total weight of the composition. Preferably, the glucoside emulsifier is present in an amount about 0.5 wt. % to about 1.6 wt. % of the total weight of the composition. More preferably, the glucoside emulsifier is present in an amount about 0.6 wt. % to about 1.3 wt. % of the total weight of the composition.

The compositions of the present invention also include water. Water is present in an amount about 45 wt. % to about 75 wt. %, and preferably about 50 wt. % to about 65 wt. %, of the total weight of the sunscreen composition.

In addition to the one or more glucoside emulsifiers, one or more additional emulsifiers may also be included in the sunscreen compositions of the present invention. The one or more additional emulsifiers, in conjunction with the one or more glucoside emulsifiers, enable two or more immiscible liquids to be combined homogeneously, while increasing the viscosity of the composition. Moreover, the emulsifiers act to stabilize the composition.

One or more additional emulsifiers that can be used in the present invention include, for example, butylated PVP, cetyl alcohol, cetearyl alcohol, behenyl alcohol, glyceryl stearate, glyceryl stearate citrate, sodium dicocoylethylenediamine PEG-15 sulfate, sodium lauroyl lactylate, sodium lauroyl sarcosinates, lecithin, sodium acrylate/sodium acryloyldimethyltaurate copolymer, diethylhexyl napthalate, sorbitan oleate, sorbitan sesquioleate, sorbitan isostearate, sorbitan trioleate, polyglyceryl-3-diisostearate, polyglycerol esters of oleic/isostearic acid, polyglyceryl-6 hexaricinolate, polyglyceryl-4-oleate, polygylceryl-4 oleate/PEG-8 propylene glycol cocoate, oleamide DEA, sodium glyceryl oleate phosphate, hydrogenated vegetable glycerides phosphate, or any mixtures thereof.

The preferred additional emulsifiers are cetyl alcohol, cetearyl alcohol, behenyl alcohol, glyceryl stearate, glyceryl stearate citrate, sodium dicocoylethylenediamine PEG-15 sulfate, sodium lauroyl lactylate, sodium lauroyl sarcosinates, lecithin, butylated PVP, cetyl alcohol, sodium acrylate/sodium acryloyldimethyltaurate copolymer, diethylhexyl napthalate, or any mixtures thereof.

The amount of additional emulsifier present in a sunscreen composition of the present invention is about 0.01 wt. % to about 5 wt. % of the total weight of the composition. Preferably, one or more emulsifiers in an amount about 0.05 wt. % to about 3 wt. % of the total weight of the composition are used.

The present composition may include one or more emollients. An emollient provides a softening or soothing effect on the skin surface and is generally considered safe for topical use. It also helps control the rate of evaporation and the tackiness of the sunscreen composition.

Suitable emollients include, for example, di-PPG-3 myristyl ether adipate, dipentaerythritol hexa $C_{5-9}$ acid esters, cyclomethicone, dimethicone, dicapryl maleate, caprylic/capric triglyceride, mineral oil, lanolin oil, coconut oil, cocoa butter, olive oil, aloe extracts such as aloe vera, jojoba oil, castor oil, fatty acid such as oleic and stearic, fatty alcohol such as cetyl and hexadecyl (ENJAY), diisopropyl adipate, hydroxybenzoate esters, benzoic acid esters of $C_9$-$C_{15}$ alcohols, isononyl iso-nonanoate, alkanes such as mineral oil, silicone such as dimethyl polysiloxane, ether such as polyoxypropylene butyl ether and polyoxypropylene cetyl ether, $C_{12}$-$C_{15}$ alkyl benzoate, or any mixtures thereof.

The preferred emollients are di-PPG-3 myristyl ether adipate, dipentaerythritol hexa $C_{5-9}$ acid esters, or any mixtures thereof.

The total amount of emollient present in the sunscreen composition is typically about 0.10 wt. % to about 30 wt. % of the total weight of the composition. The preferred amount of emollient is about 1 wt. % to about 20 wt. %.

As stated above, the feel of the sunscreen composition upon application to the skin may be the ultimate consideration of a consumer when purchasing a sunscreen. Moreover, a smooth, silky sunscreen composition may be more uniformly applied over the skin. To further enhance the feel of the sunscreen compositions of the present invention when applied to the skin, a skin-feel additive may be included. Suitable skin-feel additives include, for example, synthetic polymers, silicones, esters, particulates, or any mixtures thereof. Preferably, the skin-feel additive is a synthetic polymer, tribehenin, or any mixtures thereof. An example of a suitable synthetic polymer is nylon-12. Nylon-12 includes microscopic nylon beads, which act like ball bearings on the skin. Therefore, when the composition is applied to the skin, an enhanced silky, smooth feeling results and the composition can be applied evenly over the skin. Also, the nylon-12 has unexpectedly been found to absorb the oil in the sunscreens upon application. Thus, the nylon-12 adds slip to the composition without imparting an undesirable greasy feel.

Preferably, the skin-feel additive is present in a sunscreen composition in an amount about 0.10 wt. % to about 5 wt. % of the total weight of the composition. More preferably, it is present in an amount about 0.30 wt. % to about 0.70 wt. % of the total weight of the composition.

The pH of the compositions of the present invention may be adjusted by one or more basic pH adjusters and/or chelating agents. For example, sodium hydroxide, triethanolamine, trisodium ethylenediaminetetraacetic acid, or any mixtures thereof are suitable pH adjusters/chelating agents that may be included in the sunscreen compositions of the present invention.

An effective amount of a pH adjuster and/or chelating agent that may be included to adjust the pH of the final composition to about 3 to about 9. Preferably, the pH is adjusted to about 6 to about 8.

A moisturizing agent, such as a humectant, may be used in the compositions of the present invention. Suitable humectants include, but are not limited to, glycerin, polyethylene glycol, polypropylene glycol, sorbitol, PEG-4, or any mixtures thereof.

One or more moisturizing agents are optionally included in the compositions of the present invention in an amount about 0.1 wt. % to about 1 wt. % of the total weight of the composition. Preferably, about 0.25 wt. % to about 0.75 wt. % of one or more moisturizing agents may be used in the composition.

Another component that may be used in a sunscreen composition of the present invention is a film former/waterproofing agent. The film former/waterproofing agent is a hydrophobic material that imparts film forming and waterproofing characteristics to the emulsion. One such agent is polyethylene, which is available from New Phase Technologies as PERFORMALENE® 400, a polyethylene having a molecular weight of 400. Another suitable water-proofing agent is polyethylene 2000 (molecular weight of 2000), which is available from New Phase Technologies as PERFORMALENE® 2000. Yet, another suitable film former/waterproofing agent is synthetic wax, also available from New Phase Technologies as PERFORMA® V-825. Still yet another suitable film former/waterproofing agent is octadecene/MA copolymer. One or more film formers/waterproofing agents may be present in a composition of the present invention in an amount about 0.1 wt. % to about 5 wt. % of the total weight of the composition.

Optionally, one or more preservatives may be included in a composition of the present invention. The preservative protects the composition from microbial contamination and/or oxidation. As such, the preservative can include an antioxidant. Preservatives, such as methyldibromo glutaronitrile, methylchloroisothiazolinone, phenoxyethanol, diazolidinyl urea, iodopropynyl butylcarbamate, chloromethylisothiazolinone, methylisothiazolinone, vitamin E and its derivatives including vitamin E acetate, vitamin C, butylated hydroxytoluene, methylparaben, or any mixtures thereof, may be included as a preservative in a composition of the present invention. In one embodiment, a composition of the present invention may have a combination of methyldibromo glutaronitrile, methylchloroisothiazolinone, methylisothiazolinone, and phenoxyethanol, available from Schulke and Mayr GMBH and Co., KG as EUXYL K727.

About 0.01 wt. % to about 1 wt. % of preservative may be included in a composition of the present invention. Preferably, the present composition has one or more preservatives in an amount that totals about 0.05 wt. % to about 0.50 wt. % of the total weight of the composition.

The sunscreen compositions of the present invention may also have other optional additives. For instance, one or more fragrances, colorants, plant extracts, absorbents, thickeners/rheology modifiers, salicylic acid, alpha and beta hydroxy acids, vitamins including vitamins A, C, and E, retinol, retinol palmitate, vitamin E acetate, tocopherol, vitamin A palmitate, vitamin E palmitate, or any mixtures thereof, may be included in the sunscreen compositions.

Examples of suitable thickeners/rheology modifiers include, but are not limited to, one or more gums, such as xanthan gum; glyceryl stearate; acrylate polymers, such as acrylates/$C_{10-30}$ alkyl acrylate crosspolymer; or any combinations thereof.

The components of the present invention may be combined to form a stable oil-in-water emulsion. The sunscreen is incorporated into the oil phase and later combined with water with the help of the one or more emulsifiers. The process used to manufacture the composition of the present invention must be capable of forming a homogeneous composition that can be spread into a film.

In one embodiment of the present invention, the sunscreen composition includes about 6 wt. % to about 12 wt. % of one or more of the following sunscreen agents: octyl methoxycinnamate, octyl salicylate, butyl methoxydibenzoylmethane, or any mixtures thereof; and about 4 wt. % to about 6 wt. % of MONTANOV® 82. This composition has been found to have an enhanced soft, silky feel when applied to the skin. In addition, this composition has a SPF of at least 15. In a more preferred embodiment, this composition also includes about 0.25 wt. % to about 1 wt. % of nylon-12, which further enhances the soft, silky feel of the composition when applied to the skin.

In another embodiment of the present invention, the sunscreen composition includes about 15 wt. % to about 25 wt. % of one or more of the following sunscreen agents: octyl methoxycinnamate, octyl salicylate, benzophenone-3, butyl methoxydibenzoylmethane, or any mixtures thereof; and about 4 wt. % to about 6 wt. % of MONTANOV® 82. This composition also has been found to have an enhanced soft, silky feel when applied to the skin. In addition, this composition has a SPF of at least 30. In a more preferred embodiment, this composition also includes about 0.25 wt. % to about 1 wt. % of nylon-12, which further enhances the soft, silky feel of the composition when applied to the skin.

In yet another embodiment of the present invention, the sunscreen composition includes about 20 wt. % to about 30 wt. % of one or more of the following sunscreen agents: octyl methoxycinnamate, octyl salicylate, benzophenone-3, zinc oxide mixed with alkyl benzoate, or any mixtures thereof; and about 4 wt. % to about 6 wt. % of MONTANOV® 82. This composition has been found to also have an enhanced soft, silky feel when applied to the skin. In addition, this composition has a SPF of at least 50.

In still yet another embodiment of the present invention, a sunscreen composition includes about 6 wt. % to about 12 wt. % of one or more sunscreens and about 0.6 wt. % to about 1.3 wt. % lauryl glucoside. The sunscreens may be octyl methoxycinnamate, octyl salicylate, butyl methoxydibenzoylmethane, octocrylene, benzophenone-3, or any mixtures thereof. This composition has been found to also have an enhanced soft, silky feel when applied to the skin. In addition, this composition has a SPF of at least 15.

In a further embodiment of the present invention, a sunscreen composition includes about 15 wt. % to about 25 wt. % of one or more sunscreens and about 0.6 wt. % to about 1.3 wt. % lauryl glucoside. The sunscreens may be octyl methoxycinnamate, octyl salicylate, butyl methoxydibenzoylmethane, octocrylene, benzophenone-3, or any mixtures thereof. This composition has been found to also have an enhanced soft, silky feel when applied to the skin. In addition, this composition has a SPF of at least 30.

In yet a further embodiment of the present invention, a sunscreen composition includes about 20 wt. % to about 30 wt. % of one or more sunscreens and about 0.6 wt. % to about 1.3 wt. % lauryl glucoside. The sunscreens may be octyl methoxycinnamate, octyl salicylate, butyl methoxydibenzoylmethane, octocrylene, benzophenone-3, zinc oxide mixed with $C_{12-15}$ alkyl benzoate, titanium dioxide, or any mixtures thereof. This composition has been found to also have an enhanced soft, silky feel when applied to the skin. In addition, this composition has a SPF of at least 50.

The sunscreen compositions may be prepared by using techniques and methods well known in the art. In general, ingredients are incorporated by mixing and applying heat if necessary, until the composition is uniform and homogeneous. The composition may be homogenized to ensure homogeneity and to build the proper viscosity. The sunscreen compositions of the present invention are then packaged as a lotion in any package or container suitable for a sunscreen composition.

EXAMPLE 1

Table 1 illustrates an example of a sunscreen composition according to the present invention.

TABLE 1

Composition A

| Ingredient Name | Phase (Aqueous or Oil) | wt % |
|---|---|---|
| Water | A | 12 |
| Glycerin | A | 1.2 |
| Xanthan gum | A | 0.05 |
| Lauryl glucoside[1] | A | 2.45 |
| Sodium lauroyl sarcosinate | A | 1.6 |
| PEG-7 methyl ether | O | 3 |
| Di-PPG-3 myristyl ether adipate | O | 2 |
| Dipentaerythritol hexa $C_{5-9}$ acid esters | O | 1 |
| Octisalate | O | 5 |
| Octinoxate | O | 7.5 |
| Octocrylene | O | 1.2 |
| Oxybenzone | O | 3 |
| Avobenzone | O | 1.5 |
| Behenyl alcohol & glyceryl stearate & glyceryl stearate citrate & sodium dicocoylethylenediamine PEG-15 sulfate[2] | O | 0.65 |
| Glyceryl stearate & cetearyl alcohol & sodium lauroyl lactylate & lecithin[3] | O | 0.15 |
| Tribehenin | O | 2 |
| Glyceryl stearate | O | 2 |
| Octadecene/MA copolymer | O | 1.5 |
| Water | A | 51 |
| Acrylates/$C_{10-30}$ alkyl acrylate crosspolymer | A | 0.3 |

TABLE 1-continued

Composition A

| Ingredient Name | Phase (Aqueous or Oil) | wt % |
|---|---|---|
| Xanthan gum | A | 0.3 |
| Trisodium edta | A | 0.1 |
| Methyldibromo glutaronitrile & methylchloroisothizolinone & methylisothiazolinone & phenoxyethanol[4] | A | 0.2 |
| Triethanolamine | A | 0.3 |
| Total: | | 100 |

[1]PLANTAREN 1200N (Cognis Corporation), which is 50% active (1.225 wt. % lauryl glucoside).
[2]CERALUTION H (Sasol)
[3]BIOBASE EP (Tri-K)
[4]Euxyl K727 (Schulke and Mayr GMBH and Co., KG)

EXAMPLE 2

Table 2 illustrates a comparative example composition.

TABLE 2

Composition B

| Ingredient Name | WEIGHT PERCENTAGE (wt. %) |
|---|---|
| Water (Purified, USP) | 60.5 |
| Octinoxate | 7.5 |
| Oxybenzone | 5.25 |
| Octisalate | 4.75 |
| Stearic Acid | 4.72 |
| Stearyl Alcohol | 2.6 |
| Polyethylene | 2.4 |
| Methyl Acetyl Ricinoleate | 2.3 |
| Isopropyl Myristate (and) Titanium Dioxide (and) Polyhydroxystearic Acid (and) Aluminum Stearate (and) Alumina | 2.05 |
| $C_{12-15}$ Alkyl Benzoate (and) Titanium Dioxide (and) Alumina (and) Polyhydroxystearic Acid (and) Silica | 2.05 |
| Glyceryl Stearate | 1.5 |
| PEG-40 Castor Oil | 1.4 |
| Magnesium Aluminum Silicate | 0.85 |
| Silica | 0.57 |
| Octadecene/MA Copolymer | 0.3 |
| Ceteareth-20 | 0.3 |
| PEG-7 Glyceryl Cocoate | 0.26 |
| Imidazolidinyl Urea | 0.15 |
| DMDH Hydantoin (and) Iodopropynyl | 0.1 |
| Quaternium-15 | 0.1 |
| Triethanolamine | 0.1 |
| Tocopherol | 0.1 |
| Hydroxyethylcellulose | 0.08 |
| Trisodium EDTA | 0.05 |
| Hydrolyzed Collagen | 0.01 |
| Aloe Barbadensis Leaf Juice | 0.01 |
| Total: | 100 |

EXAMPLE 3

The emulsion particle size and in-vitro of Compositions A and B were measured. The emulsion particle size was measured using a particle size analyzer (Horiba Model No. LA-920 "Particle Size Analyzer"). The in-vitro SPF was measured using a Labsphere with Vitro Skin substrate. The emulsion particle size of Composition A was 0.8688 microns with an in-vitro SPF of 26. The emulsion particle size of Composition B was 4.5099 microns with an in-vitro SPF of 19. The smaller emulsion particle size of Composition A corresponds to a higher SPF than that of Composition B, which has a similar level of UVB sunscreen actives as Composition A. The UVA sunscreen active, avobenzone, in Composition B does not contribute to SPF.

EXAMPLE 4

The yield stress values of Compositions A and B were measured using a rheometer (Rheometric Scientific, Model No. SR5). Composition A had a yield stress value of 194 Pa. Composition B had a yield stress value of 547 Pa. These values indicate that the emulsion of Composition A, having lauryl glucoside, breaks easier into its oil phase and aqueous phase when applied to the skin. Composition A has a very quick absorbing, elegant feel when applied to the skin.

EXAMPLE 5

The waterproofing of Compositions A and B was analyzed. The in-vitro SPF of a sample of each composition was measured. This initial SPF measurement is the static in-vitro SPF. Next, VWR (very water resistant) SPF was measured by placing each sample in a separate 600 mL beaker. The beaker was then filled with deionized water at about 21 to 24° C. until the water covered the Vitro Skin. The water was stirred at about 400 rpm for 80 minutes. The Vitro Skin was then removed and allowed to air dry for 60 minutes. The Vitro Skin was then placed in a hydration chamber for 12 to 24 hours and the VWR SPF was measured using the Labsphere. Table 3 indicates the results of static SPF and VWR SPF for Compositions A and B.

TABLE 3

Static SPF and VWR SPF for Compositions A and B

|  | SPF (static) | VWR SPF |
|---|---|---|
| Composition A | 57 | 47 |
| Composition B | 37.9 | 31.5 |

Composition A retains significant SPF while using less film-forming/waterproofing agents than Composition B (Composition A: 1.5 wt. % to Composition B: 2.7 wt. %). Composition A also uses less emulsifier (3.625 wt. %) than Composition B (6.42 wt. %) while still holding a large oil phase (30.5 wt. %).

Having thus described the present invention with particular reference to preferred embodiments thereof, it will be apparent that various changes and modifications may be made therein without departing from the spirit and scope of the present invention as defined in the appended claims.

What is claimed is:

1. A sunscreen composition comprising:
    (a) at least one sunscreen agent; and
    (b) at least one lauryl glucoside emulsifier,
    wherein said at least one lauryl glucoside emulsifier imparts an enhanced soft, silky feel to the composition.

2. The composition of claim 1, wherein said at least one sunscreen agent is selected from the group consisting of para-aminobenzoic acid (PABA), avobenzone, benzophenone-1, benzophenone-2, benzophenone-3, benzophenone-4, benzophenone-6, benzophenone-8, benzophenone-12, methoxycinnamate, ethyl dihydroxypropyl-PABA, glyceryl PABA, homosalate, methyl anthranilate, octocrylene, octyl dimethyl PABA, octyl methoxycinnamate, octyl salicylate, PABA, 2-phenylbenzimidazole-5-sulphonic acid, triethanolamine salicylate, 3-(4-methylbenzylidene)-camphor, red petrolatum, zinc oxide, titanium dioxide, 3-(4-methylbenzyldine) boran-2-one(methylbenzindinecamphor), benzotriazole, phenylbenzimidazole-5-sulfonic acid, methylene bis-benzotrizolyl tetramethylbutyl phenol, and any combinations thereof.

3. The composition of claim 1, wherein said at least one sunscreen agent is selected from the group consisting of avobenzone, benzophenone-3, octyl methoxycinnamate, octyl salicylate, homosalate, zinc oxide, octocrylene, avobenzone, titanium dioxide, and any combinations thereof.

4. The composition of claim 1, wherein said at least one sunscreen agent is about 1 wt. % to about 40 wt. % of the total weight of the composition.

5. The composition of claim 1, wherein said at least one lauryl glucoside emulsifier is about 0.05 wt. % to about 10 wt. % of the total weight of the composition.

6. The composition of claim 1, wherein said at least one lauryl glucoside emulsifier is about 0.5 wt. % to about 1.6 wt. % of the total weight of the composition.

7. The composition of claim 1, further comprising one or more additional emulsifiers other than a glucoside emulsifier.

8. The composition of claim 7, wherein said one or more additional emulsifiers are selected from the group consisting of butylated PVP, cetyl alcohol, cetearyl alcohol, behenyl alcohol, glyceryl stearate, glyceryl stearate citrate, sodium dicocoylethylenediamine PEG-15 sulfate, sodium lauroyl lactylate, sodium lauroyl sarcosinates, lecithin, sodium acrylate/sodium acryloyldimethyltaurate copolymer, diethylhexyl napthalate, sorbitan oleate, sorbitan sesquioleate, sorbitan isostearate, sorbitan trioleate, polyglyceryl-3-diisostearate, polyglycerol ester of oleic/isostearic acid, polyglyceryl-6 hexaricinolate, polyglyceryl-4-oleate, polygylceryl-4 oleate/PEG-8 propylene glycol cocoate, oleamide DEA, sodium glyceryl oleate phosphate, hydrogenated vegetable glycerides phosphate, and any combinations thereof.

9. The composition of claim 7, wherein said one or more additional emulsifiers are selected from the group consisting of cetyl alcohol, cetearyl alcohol, behenyl alcohol, glyceryl stearate, glyceryl stearate citrate, sodium dicocoylethylenediamine PEG-15 sulfate, sodium lauroyl lactylate, sodium lauroyl sarcosinates, lecithin, and any combinations thereof.

10. The composition of claim 1, further comprising one or more emollients.

11. The composition of claim 10, wherein said one or more emollients is selected from the group consisting of di-PPG-3 myristyl ether adipate, dipentaerythritol hexa $C_{5-9}$ acid esters, cyclomethicone, dimethicone, dicapryl maleate, caprylic/capric triglyceride, mineral oil, lanolin oil, coconut oil, cocoa butter, olive oil, aloe extracts, jojoba oil, castor oil, fatty acid, fatty alcohol, diisopropyl adipate, hydroxybenzoate ester, benzoic acid ester of $C_9$-$C_{15}$ alcohols, isononyl isononanoate, alkane, silicone, ether, $C_{12}$-$C_{15}$ alkyl benzoate, and any combinations thereof.

12. The composition of claim 10, wherein said one or more emollients is selected from the group consisting of di-PPG-3 myristyl ether adipate, dipentaerythritol hexa $C_{5-9}$ acid esters, and any combinations thereof.

13. The composition of claim 11, wherein said one or more emollients are present in an amount about 0.10 wt. % to about 30 wt. % of the total weight of the composition.

14. The composition of claim 1, further comprising water.

15. The composition of claim 14, wherein said water is present in an amount about 45 wt. % to about 75 wt. % of the total weight of the composition.

16. The composition of claim 1, further comprising one or more additional components selected from the group consisting of skin-feel additive, moisturizing agent, film former/waterproofing agent, pH adjuster/chelating agent, preservative, and any combinations thereof.

17. The composition of claim 16, wherein said skin-feel additive is selected from the group consisting of synthetic polymers, tribehenin, silicones, esters, particulates, and any combinations thereof.

18. The composition of claim 17, wherein said skin-feel additive is tribehenin.

19. The composition of claim 17, wherein said skin-feel additive is present in an amount about 0.10 wt. % to about 5 wt. % of the total weight of the composition.

20. The composition of claim 16, wherein said moisturizing agent is a humectant.

21. The composition of claim 20, wherein said humectant is selected from the group consisting of glycerin, polyethylene glycol, polypropylene glycol, sorbitol, PEG-4, and any combinations thereof.

22. The composition of claim 16, wherein said moisturizing agent is present in an amount about 0.10 wt. % to about 1 wt. % of the total weight of the composition.

23. The composition of claim 16, wherein said film former/waterproofing agent is selected from the group consisting of polyethylene, octadecene/MA copolymer, synthetic wax, and any combinations thereof.

24. The composition of claim 16, wherein said film former/waterproofing agent is present in an amount about 0.10 wt. % to about 5 wt. % of the total weight of the composition.

25. The composition of claim 16, wherein said pH adjuster/chelating agent is selected from the group consisting of sodium hydroxide, triethanolamine, trisodium ethylenediaminetetraacetic acid, and any combinations thereof.

26. The composition of claim 16, wherein said preservative is selected from the group consisting of methyldibromo glutaronitrile, methylchloroisothiazolinone, phenoxyethanol, diazolidinyl urea, iodopropynyl butylcarbamate, chloromethylisothiazolinone, methylisothiazolinone, vitamin E and its derivatives, vitamin C, butylated hydroxytoluene, methylparaben, and any combinations thereof.

27. A sunscreen composition comprising:
(a) about 6 wt. % to about 12 wt. % of one or more sunscreens; and
(b) about 0.6 wt. % to about 1.3 wt. % lauryl glucoside,
wherein said lauryl glucoside imparts a soft, silky feel to the composition when applied to a user's skin.

28. The composition of claim 27, wherein said one or more sunscreens are selected from the group consisting of octyl methoxycinnamate, octyl salicylate, butyl methoxydibenzoylmethane, octocrylene, benzophenone-3, and any combinations thereof.

29. The composition of claim 27, further comprising one or more additional components selected from the group consisting of emulsifier other than glucoside, emollient, skin-feel additive, moisturizing agent, film former/waterproofing agent, pH adjuster/chelating agent, preservative, and any combinations thereof.

30. The composition of claim 27, wherein the composition has a SPF of at least 15.

31. A sunscreen composition comprising:
(a) about 15 wt. % to about 25 wt. % of one or more sunscreens; and
(b) about 0.6 wt. % to about 1.3 wt. % lauryl glucoside,
wherein said lauryl glucoside imparts a soft, silky feel to the composition when applied to a user's skin.

32. The composition of claim 31, wherein said one or more sunscreens are selected from the group consisting of octyl methoxycinnamate, octyl salicylate, octocrylene, benzophenone-3, butyl methoxydibenzoylmethane, and any combinations thereof.

33. The composition of claim 31, further comprising one or more additional components selected from the group consisting of emulsifier other than glucoside, emollient, skin-feel additive, moisturizing agent, film former/waterproofing agent, pH adjuster/chelating agent, preservative, and any combinations thereof.

34. The composition of claim 31, wherein the composition has a SPF of at least 30.

35. A sunscreen composition comprising:
(a) about 20 wt. % to about 30 wt. % of one or more sunscreens; and
(b) about 0.6 wt. % to about 1.3 wt. % lauryl glucoside,
wherein said lauryl glucoside imparts a soft, silky feel to the composition when applied to a user's skin.

36. The composition of claim 35, wherein said one or more sunscreens are selected from the group consisting of octyl methoxycinnamate, octyl salicylate, octocrylene, benzophenone-3, butyl methoxydibenzoylmethane, zinc oxide mixed with $C_{12-15}$ alkyl benzoate, titanium dioxide, and any combinations thereof.

37. The composition of claim 35, further comprising one or more additional components selected from the group consisting of emulsifier other than glucoside, emollient, skin-feel additive, moisturizing agent, film former/waterproofing agent, pH adjuster/chelating agent, preservative, and any combinations thereof.

38. The composition of claim 35, wherein the composition has a SPF of at least 50.

* * * * *